(12) United States Patent
Huizenga

(10) Patent No.: US 8,688,477 B1
(45) Date of Patent: Apr. 1, 2014

(54) METHOD, SYSTEM, AND COMPUTER PROGRAM PRODUCT FOR DETERMINING A NARCOTICS USE INDICATOR

(75) Inventor: James Huizenga, Dayton, OH (US)

(73) Assignee: National Assoc. of Boards of Pharmacy, Mount Prospect, IL (US)

(*) Notice: Subject to any disclaimer, the term of this patent is extended or adjusted under 35 U.S.C. 154(b) by 107 days.

(21) Appl. No.: 13/234,777

(22) Filed: Sep. 16, 2011

Related U.S. Application Data (60) Provisional application No. 61/383,927, filed on Sep. 17, 2010.

(51) Int. Cl.
*A61B 5/00* (2006.01)
*G06F 19/00* (2011.01)

(52) U.S. Cl.
USPC .............................................. 705/3

(58) Field of Classification Search
USPC ........................................ 705/2, 3
See application file for complete search history.

(56) References Cited

U.S. PATENT DOCUMENTS

| | | | |
|---|---|---|---|
| 4,975,840 A | 12/1990 | DeTore et al. | |
| 5,550,734 A | 8/1996 | Tarter et al. | |
| 5,583,758 A | 12/1996 | McIlroy et al. | |
| 5,679,938 A | 10/1997 | Templeton et al. | |
| 5,679,940 A | 10/1997 | Templeton et al. | |
| 5,764,923 A | 6/1998 | Tallman et al. | |
| 5,809,478 A | 9/1998 | Greco et al. | |
| 5,833,599 A | 11/1998 | Schrier et al. | |
| 5,867,821 A | 2/1999 | Ballantyne et al. | |
| 6,024,699 A | 2/2000 | Surwit et al. | |
| 6,088,686 A | 7/2000 | Walker et al. | |
| 6,119,103 A | 9/2000 | Basch et al. | |
| 6,151,581 A | 11/2000 | Kraftson et al. | |
| 6,202,053 B1 | 3/2001 | Christiansen et al. | |
| 6,421,650 B1 | 7/2002 | Goetz et al. | |
| 6,452,613 B1 | 9/2002 | Lefebvre et al. | |
| 6,456,979 B1 | 9/2002 | Flagg | |
| 6,484,144 B2 | 11/2002 | Martin et al. | |
| 6,533,724 B2 | 3/2003 | McNair | |
| 6,647,374 B2 | 11/2003 | Kansal | |

(Continued)

OTHER PUBLICATIONS

McKesson, New McKesson Automation Software Release Enables Advance Analysis for Improved Product Performance, Dec. 3, 2009, McKesson Press Release on Pharmacychoice.com.

(Continued)

*Primary Examiner* — John Pauls
*Assistant Examiner* — Trang Nguyen
(74) *Attorney, Agent, or Firm* — Marshall, Gerstein & Borun LLP; Randall G. Rueth (57) ABSTRACT

A method, system, and computer program product for determining a narcotics use indicator to enable a physician, or other prescriber, to quickly review a numerical score that reflects a patient's past drug use and is indicative of proper, or improper, future drug use. This score analyzes many aspects of a patient's past activities to determine multiple individual indicator values that may be selectively weighted to create a final narcotics use indicator. Such individual indicator values may include a usage related indicator factoring in the patient's past drug use, particularly the type of narcotics and controlled substances used; an instruction related indicator that may consider the patient's past use of prescribers, quantity of prescriptions, or the number of open prescriptions from different prescribers; a dispensing related indicator that examines a patient's use of pharmacies, in filling prescriptions; or even an auxiliary indicator that may reflect the patient's number of active prescriptions.

23 Claims, 9 Drawing Sheets

(56) References Cited

U.S. PATENT DOCUMENTS

| | | |
|---|---|---|
| 6,839,690 B1 | 1/2005 | Foth et al. |
| 6,950,807 B2 | 9/2005 | Brock |
| 7,054,758 B2 | 5/2006 | Gill-Garrison et al. |
| 7,097,617 B1 | 8/2006 | Smith |
| 7,107,241 B1 | 9/2006 | Pinto |
| 7,236,952 B1 | 6/2007 | D'Zmura |
| 7,246,740 B2 | 7/2007 | Swift et al. |
| 7,251,625 B2 | 7/2007 | Anglum |
| 7,296,734 B2 | 11/2007 | Pliha |
| 7,306,562 B1 | 12/2007 | Baykal |
| 7,319,971 B2 | 1/2008 | Abrahams et al. |
| 7,324,954 B2 | 1/2008 | Calderaro et al. |
| 7,343,308 B1 | 3/2008 | Rojewski et al. |
| 7,346,575 B1 | 3/2008 | Ahles et al. |
| 7,386,503 B2 | 6/2008 | Belyi |
| 7,386,506 B2 | 6/2008 | Aoki et al. |
| 7,398,218 B1 | 7/2008 | Bernaski et al. |
| 7,403,922 B1 | 7/2008 | Lewis et al. |
| 7,503,488 B2 | 3/2009 | Davis |
| 7,593,892 B2 | 9/2009 | Balk et al. |
| 7,593,895 B2 | 9/2009 | Belyi |
| 7,620,597 B2 | 11/2009 | Eze |
| 7,630,932 B2 | 12/2009 | Danaher et al. |
| 7,647,263 B2 | 1/2010 | Daul et al. |
| 7,653,555 B2 | 1/2010 | Wiese |
| 7,653,590 B1 | 1/2010 | Kroon et al. |
| 7,653,593 B2 | 1/2010 | Zarikian et al. |
| 7,664,670 B1 | 2/2010 | Weiss |
| 7,668,776 B1 | 2/2010 | Ahles |
| 7,680,719 B1 | 3/2010 | Brady et al. |
| 7,685,000 B1 | 3/2010 | Petit et al. |
| 7,689,494 B2 | 3/2010 | Torre et al. |
| 7,698,157 B2 | 4/2010 | Ghouri |
| 7,698,202 B2 | 4/2010 | Stubbs et al. |
| 7,698,213 B2 | 4/2010 | Lancaster |
| 7,739,256 B2 | 6/2010 | Powell |
| 7,742,982 B2 | 6/2010 | Chaudhuri et al. |
| 7,752,020 B2 | 7/2010 | Seppanen et al. |
| 7,778,856 B2 | 8/2010 | Reynolds et al. |
| 7,778,898 B2 | 8/2010 | Rider et al. |
| 7,783,500 B2 | 8/2010 | Meyer et al. |
| 7,805,353 B2 | 9/2010 | Woodley |
| 7,813,944 B1 | 10/2010 | Luk et al. |
| 7,814,004 B2 | 10/2010 | Haggerty et al. |
| 7,814,008 B2 | 10/2010 | Choudhuri et al. |
| 7,822,670 B2 | 10/2010 | Penello |
| 7,831,494 B2 | 11/2010 | Sloan et al. |
| 7,840,484 B2 | 11/2010 | Haggerty et al. |
| 7,849,004 B2 | 12/2010 | Choudhuri et al. |
| 7,853,520 B2 | 12/2010 | Choudhuri et al. |
| 7,856,388 B1 | 12/2010 | Srivastava et al. |
| 7,860,786 B2 | 12/2010 | Blackburn et al. |
| 2003/0229519 A1 | 12/2003 | Eidex et al. |
| 2005/0228692 A1 | 10/2005 | Hodgdon |
| 2005/0234742 A1 | 10/2005 | Hodgdon |
| 2006/0004701 A1 | 1/2006 | Bacon |
| 2006/0053037 A1 | 3/2006 | Kendall et al. |
| 2006/0080251 A1 | 4/2006 | Fried et al. |
| 2006/0212386 A1 | 9/2006 | Willey et al. |
| 2006/0217824 A1* | 9/2006 | Allmon et al. .................. 700/90 |
| 2006/0242046 A1 | 10/2006 | Haggerty et al. |
| 2007/0050288 A1 | 3/2007 | Sarkar et al. |
| 2008/0004915 A1 | 1/2008 | Brown |
| 2008/0021803 A1 | 1/2008 | Ahles et al. |
| 2008/0033767 A1 | 2/2008 | Brown |
| 2008/0046268 A1 | 2/2008 | Brown |
| 2008/0086365 A1 | 4/2008 | Zollino et al. |
| 2008/0133391 A1 | 6/2008 | Kurian et al. |
| 2008/0133402 A1 | 6/2008 | Kurian et al. |
| 2008/0140438 A1 | 6/2008 | Bares |
| 2008/0162383 A1 | 7/2008 | Kraft |
| 2008/0222015 A1 | 9/2008 | Megdal et al. |
| 2008/0222027 A1 | 9/2008 | Megdal et al. |
| 2008/0222038 A1 | 9/2008 | Eden et al. |
| 2008/0228556 A1 | 9/2008 | Megdal et al. |
| 2009/0037323 A1 | 2/2009 | Feinstein et al. |
| 2009/0099959 A1 | 4/2009 | Liao et al. |
| 2009/0106054 A1 | 4/2009 | Sarel |
| 2009/0125319 A1 | 5/2009 | Craine |
| 2009/0171756 A1 | 7/2009 | De Zilwa et al. |
| 2009/0171757 A1 | 7/2009 | Feinstein et al. |
| 2009/0198610 A1 | 8/2009 | Wu et al. |
| 2009/0222308 A1 | 9/2009 | Zoldi et al. |
| 2009/0276233 A1 | 11/2009 | Brimhall et al. |
| 2009/0327120 A1 | 12/2009 | Eze et al. |
| 2010/0010930 A1 | 1/2010 | Allen et al. |
| 2010/0023448 A1 | 1/2010 | Eze |
| 2010/0049539 A1 | 2/2010 | Wiese |
| 2010/0145847 A1 | 6/2010 | Zarikian et al. |
| 2010/0211494 A1 | 8/2010 | Clements |
| 2010/0217738 A1 | 8/2010 | Sarel |
| 2010/0250430 A1 | 9/2010 | Ariff et al. |
| 2010/0268639 A1 | 10/2010 | Feinstein et al. |
| 2010/0274720 A1 | 10/2010 | Carlson et al. |
| 2010/0305993 A1 | 12/2010 | Fisher |
| 2011/0238593 A1* | 9/2011 | Hearnes, II et al. .......... 705/341 |
| 2011/0288886 A1* | 11/2011 | Whiddon et al. ................. 705/3 |

OTHER PUBLICATIONS

McKesson, McKesson Automation Decision Support, McKesson Automation Decision Support Overview Brochure.

* cited by examiner

Search Criteria: Last Name: _______ First Name: _______ DOB: _______

| Fill Date | Drug Type | Strength | Form | Qty | Days | Patient | Prescriber | Written | RX # |
|---|---|---|---|---|---|---|---|---|---|
| 11/13/2010 | ATROPINE/DIPHENOXYLATE | 0.025 MG - 2.5 MG | TAB | 100 | 25 | PAT.1 | PRESC.1 | 11/11/2010 | RX 1 |
| 10/14/2010 | APAP/HYDROCODINE BI | 500 MG - 5 MG | TAB | 40 | 20 | PAT.1 | PRESC.2 | 10/14/2010 | RX 2 |
| 09/25/2010 | ZOLPIDEM | 5 MG | TAB | 20 | 20 | PAT.1 | PRESC.3 | 09/25/2010 | RX 3 |
| 08/11/2010 | LORAZEPAM | 1 MG | TAB | 60 | 30 | PAT.1 | PRESC.1 | 08/01/2010 | RX 4 |

METHOD, SYSTEM, AND COMPUTER PROGRAM PRODUCT FOR DETERMINING A NARCOTICS USE INDICATOR

CROSS-REFERENCE TO RELATED APPLICATIONS

This application claims the benefit of U.S. provisional patent application Ser. No. 61/383,927, filed on Sep. 17, 2010, all of which is incorporated by reference as if completely written herein.

STATEMENT REGARDING FEDERALLY SPONSORED RESEARCH OR DEVELOPMENT

This invention was not made as part of a federally sponsored research or development project.

TECHNICAL FIELD

The present invention relates to predicting proper narcotic usage; particularly, to a method and system for creating a narcotics use indicator to predict the likelihood of a patient correctly using prescription drugs.

BACKGROUND OF THE INVENTION

Prescription drug abuse is the leading form of narcotic drug abuse in the US. Heroin has been replaced with prescription grade synthetic narcotics. Approximately 3% of 12 year old children in the US admit to using Vicodin in the previous year, while about 15% of 18-25 year old men and women admit to the same. It is estimated that approximately 15 million people in the US abuse prescription drugs. Emergency Departments have seen a 111% increase in the number of visits from people who are seeking narcotics for their addiction. Prescription drug abuse is the number one drug abuse problem in the US.

Healthcare entities have to deal with this problem every day (pharmacists, hospitals, providers), as do law enforcement officials and educators. One of the tools physicians, physician assistants, pharmacists, and law enforcement can use is a state based Prescription Monitoring Program, or PMP. One such example is available at ohioPMP.org. All 50 states now have, or are developing, these programs and they are usually funded at the Federal level. These programs require that pharmacists and providers who dispense medications directly report every narcotic distribution to the state PMP. The state PMP maintains a database of these "transactions." Approved providers can log into the state PMP website and retrieve a patient's narcotic use information in PDF format. This document may be 1-10 pages long and annotates very specific details about prescription usage (who, where, when, what, how much, when written, when filled, new or refill, etc.). Presumably, a prescriber, such as a physician or physician's assistant, would utilize this site whenever they were concerned about the potential for prescription drug abuse. However, prescribers use this service at a relatively low rate because it is a somewhat arduous process to navigate to the site, login, enter demographic data, wait for the report search, download the PDF and then read all of the data. Ohio reports that only 17% of prescribers in the state have even applied for access to the PMP and fewer than that use the system regularly.

SUMMARY OF THE INVENTION

A claimed method, system, and computer program product for determining a narcotics use indicator that enables a significant advance in the state of the art. A prescription database containing at least one record indicative of the prescription drug use by the patient is utilized in determining an indicator that may be used by a prescriber to quickly assess whether the patent is likely to correctly use a prescription, or possibly whether the patent is likely to abuse a prescription drug. This narcotics use indicator analyzes many aspects of a patient's past prescription drug use to determine multiple individual indicator values that may then be selectively weighted to create a final narcotics use indicator. Such individual indicator values may include a usage related indicator that may consider the patients past prescription drug use, particularly the type of narcotics and controlled substances used by the patient. A second class of potential individual indicator values is an instruction related indicator that may consider the patient's past use of prescribers, quantity of prescriptions, or the number of open prescriptions from different prescribers during a given period. A third class of potential individual indicator values is a dispensing related indicator that examines a patient's use of distribution sources, or pharmacies, in filling prescriptions. Finally, a fourth class of potential individual indicator values is an auxiliary indicator that may reflect the patient's number of active prescriptions, the frequency with which potential prescribers have requested a narcotics use indicator, or how the patient's narcotics use indicator has changed over time. At least two of these classes of individual indicator values may then be selectively weighted and transformed into a numerical score for the narcotics use indicator, as will be explained in much greater detail below.

BRIEF DESCRIPTION OF THE DRAWINGS

Without limiting the scope of the present method, system, and program, referring now to the drawings and figures:

FIG. 4 shows a table representative of data that may be contained in a patient record;

These drawings are provided to assist in the understanding of exemplary embodiments as described in more detail below and should not be construed as unduly limiting. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The claimed method, system, and computer program product for determining a narcotics use indicator enables a significant advance in the state of the art.

As previously touched upon, a prescription database (6000) may reside on a state PMP server, however one skilled in the art will appreciate that the prescription database (6000) described herein is not limited to a statewide system or a federal system, as it may be a hospital specific prescription database, a commercial prescription database, or community specific prescription database (6000). Similarly, the prescription database (6000) need not reside on a server but rather may reside on a local memory device in a standalone manner, and further, in anticipation of advances in health care IT infrastructure, the prescription database (6000) may be created for an individual patient broadly electronically querying a network of health care providers and aggregating the collected data, which may be completed in virtually real-time. Regardless of the scope, location, or creation of the prescription database (6000), it contains at least one of record (6100) indicative of the prescription drug use by the patient. One illustrative record (6100) is seen in FIG. 4. A record (6100) may contain information such as a patient ID (6105), a prescription written date (6110), a prescription expiration date (6115), a prescription period (6120), a prescriber (6145), a prescriber location (6150), a distributor (6155), a distributor location (6160), and a distribution date (6165). The record (6100) may even contain data indicative of the number of times it has been accessed, such as a record request date (6200), data indicative of who has accessed the record such as a record requester (6300) data field, as well as where the requester is located, such as a requester location (6310) data field.

The record (6100) may also contain data pertaining to the prescriptions that have been filled for a particular patient, whether they are for narcotics or controlled substances. Therefore, the record (6100) may contain data about a prescribed narcotic such as a narcotic type (6125N), a narcotic strength (6130N), a narcotic form (6135N), and a narcotic quantity (6140N). The record (6100) may contain similar information regarding prescribed controlled substances such as a controlled substance type (6125C), a controlled substance strength (6130C), a controlled substance form (6135C), and a controlled substance quantity (6140C). Thus, in these examples the element numbers for narcotics end with the letter "N" and those for controlled substances end in the letter "C", while sharing the same numerical references. These are simply examples of the data that may be contained within a record (6100) and are not all required, nor are these the only types of data that may reside in a record (6100).

Figure 5:
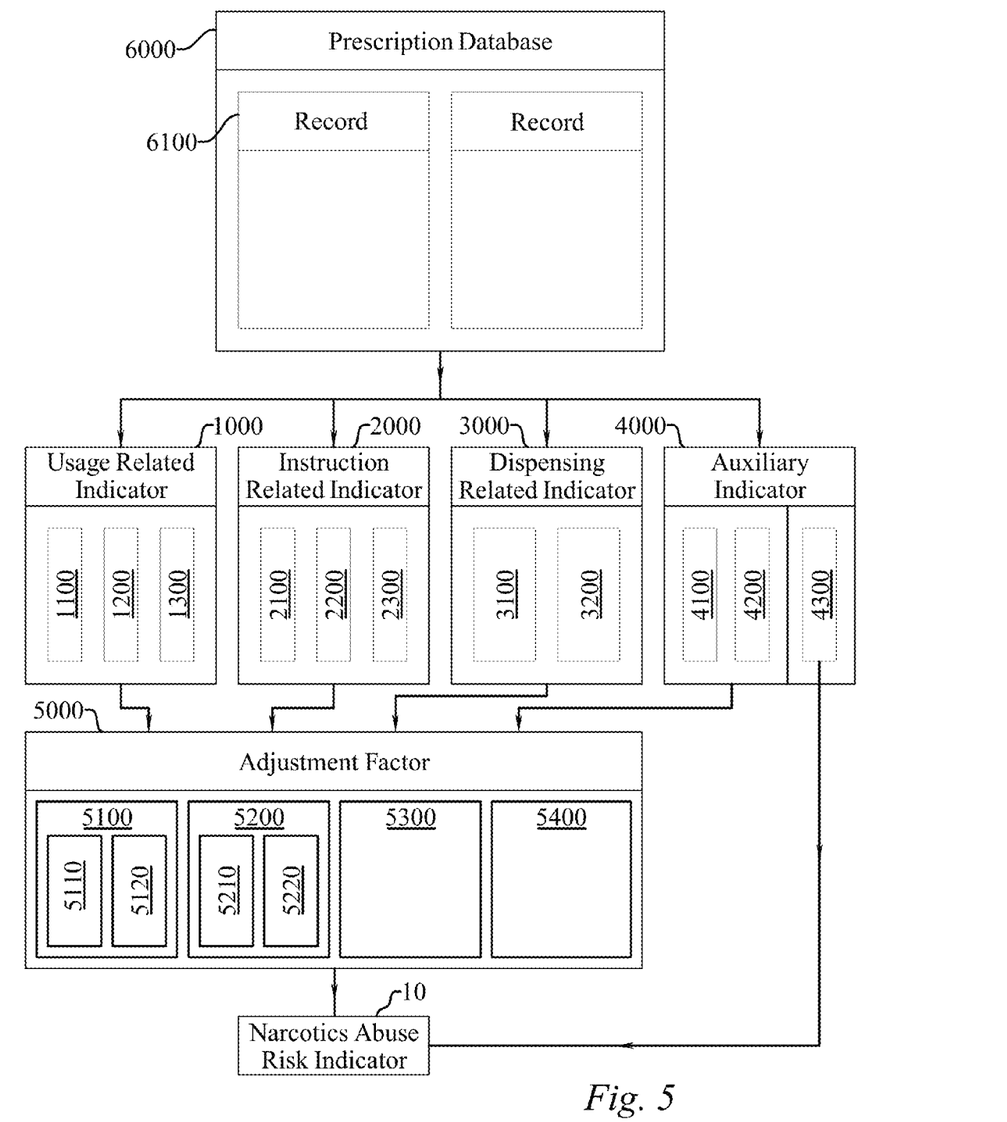
FIG. 5 shows a schematic block diagram illustrating aspects of many embodiments in a single diagram.

The present method, system, and computer program product retrieve patient specific data from a record (6100) and transforms the data into at least one indicator by comparing the patient specific data with a plurality of general population prescription drug use data. The indicator, or indicators, are then transformed into a narcotics use indicator (10) via the application of at least one adjustment factor. A diagram of one embodiment of the procedure is seen in FIG. 5 wherein at least one piece of patient specific data is retrieved from a record (6100) and is then transformed into at least one of a usage related indicator (1000), an instruction related indicator (2000), a dispensing related indicator (3000), or an auxiliary indicator (4000) by comparing the patient specific data with a plurality of general population prescription drug use data. Then at least one adjustment factor (5000) is applied to at least one of the indicators to create the narcotics use indicator (10).

In one embodiment patient specific data including at least a prescriber (6145), a distributor (6155), a narcotic type (6125N), a narcotic strength (6130N), and a narcotic quantity (6140N) is retrieved from the record (6100). Next, at least one prescription drug use processor receives this data and transforms it into at least two indicators; namely, a usage related indicator (1000) and an instruction related indicator (2000). The a usage related indicator (1000) is created by comparing at least the patient information concerning the narcotic type (6125N), the narcotic strength (6130N), and the narcotic quantity (6140N) with a plurality of general population prescription drug use data; while the instruction related indicator (2000) is created by comparing at least the patient information concerning the prescriber (6145) with the plurality of general population prescription drug use data.

The act of comparing patient specific data with the plurality of general population prescription drug use data can mean a number of things, as will be explained in greater detail later. In the big picture the comparison simply results in at least an indication of where the patient data ranks when compared to similar data that is representative of a larger population of patients. For example, one embodiment may simply identify whether the patient data is in a below normal range, a normal range, or an above normal range when compared to a larger population of patients. Alternatively, another embodiment may determine a percentile ranking of the patient data compared to the larger population of patients.

Finally, the at least one prescription drug use processor applies an adjustment factor (5000) to at least one of the usage related indicator (1000) and the instruction related indicator (2000) to create an adjusted indicator, and transforms the adjusted indicator into a narcotics use indicator (10) to display on a visual media. The narcotics use indicator (10) is created within 5 seconds of the request.

Figure 10:
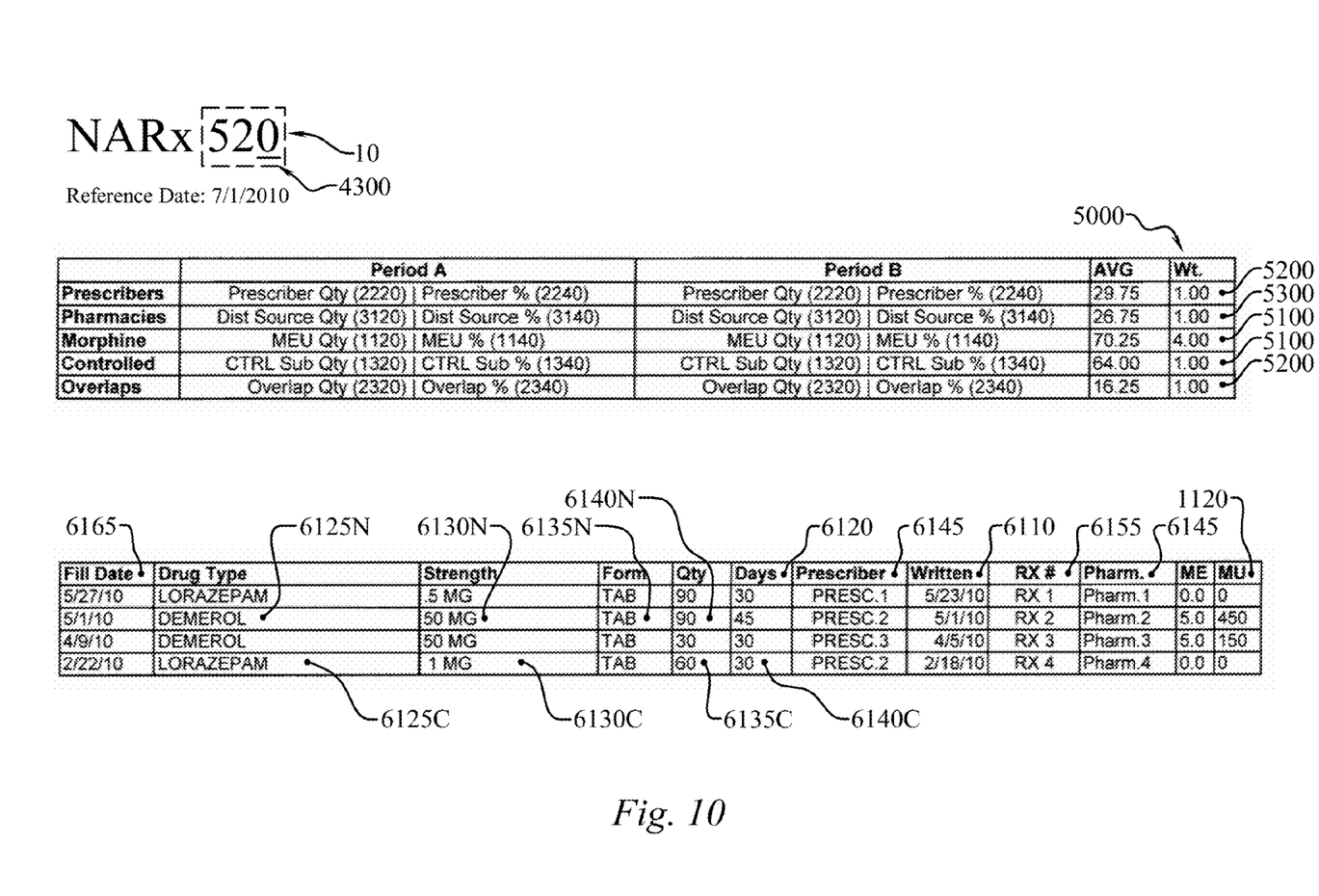
FIG. 10 shows a lower table representative of one embodiment's data that is retrieved from a patient record, and an upper table representative of several embodiments of indicators.

The embodiment above utilized only a usage related indicator (1000) and an instruction related indicator (2000). However, an example will be explained with respect to FIGS. 10 and 11 and includes a discussion of all the illustrated data and indicators for simplicity's sake only and the presence of such in this explanation is not an indication that all the data and indicators discussed are necessary. The lower table in FIG. 10 represents patient specific data that has been acquired from a record (6100) in a prescription database (6000), however it should be noted that for the previous embodiment it is not necessary that all of this patient data is retrieved from the record (6100). This particular patient had four prescriptions written between Feb. 18, 2010 and May 23, 2010 and filled between Feb. 22, 2010 and May 27, 2010; two are for the narcotic demerol and two are for the controlled substance lorazepam, which is why the demerol entry is labeled as 6125N while the lorazepam entry is labeled as 6125C (N for narcotic, C for controlled substance).

The upper table in FIG. 10 represents numerous indicators created from the patient data, as well as numerous adjustment factors (5000) used to arrive at the ultimate narcotics use indicator (10) appearing in the upper left corner of the figure as a NARx score. In one embodiment the usage related indicator (1000) may be a morphine equivalents unit indicator (1100). In this embodiment the narcotic type (6125N), the narcotic strength (6130N), and the narcotic quantity (6140N) are transformed into a morphine equivalents unit quantity (1120), seen in the far right column of the lower table. The morphine equivalents unit quantity (1120) is then compared with the plurality of general population prescription drug use data to determine a morphine equivalents unit percentile (1140) for a given morphine equivalents unit period (1110). Thus, in the upper table of FIG. 10, within the "Period A" column, which corresponds to the morphine equivalents unit period (1110), the row labeled "Morphine" contains the morphine equivalents unit quantity (1120), abbreviated MEU Qty in the table, on the left side of the hash mark, and the morphine equivalents unit percentile (1140), abbreviated MEU % in the table, on the right side of the hash mark.

Figure 11:
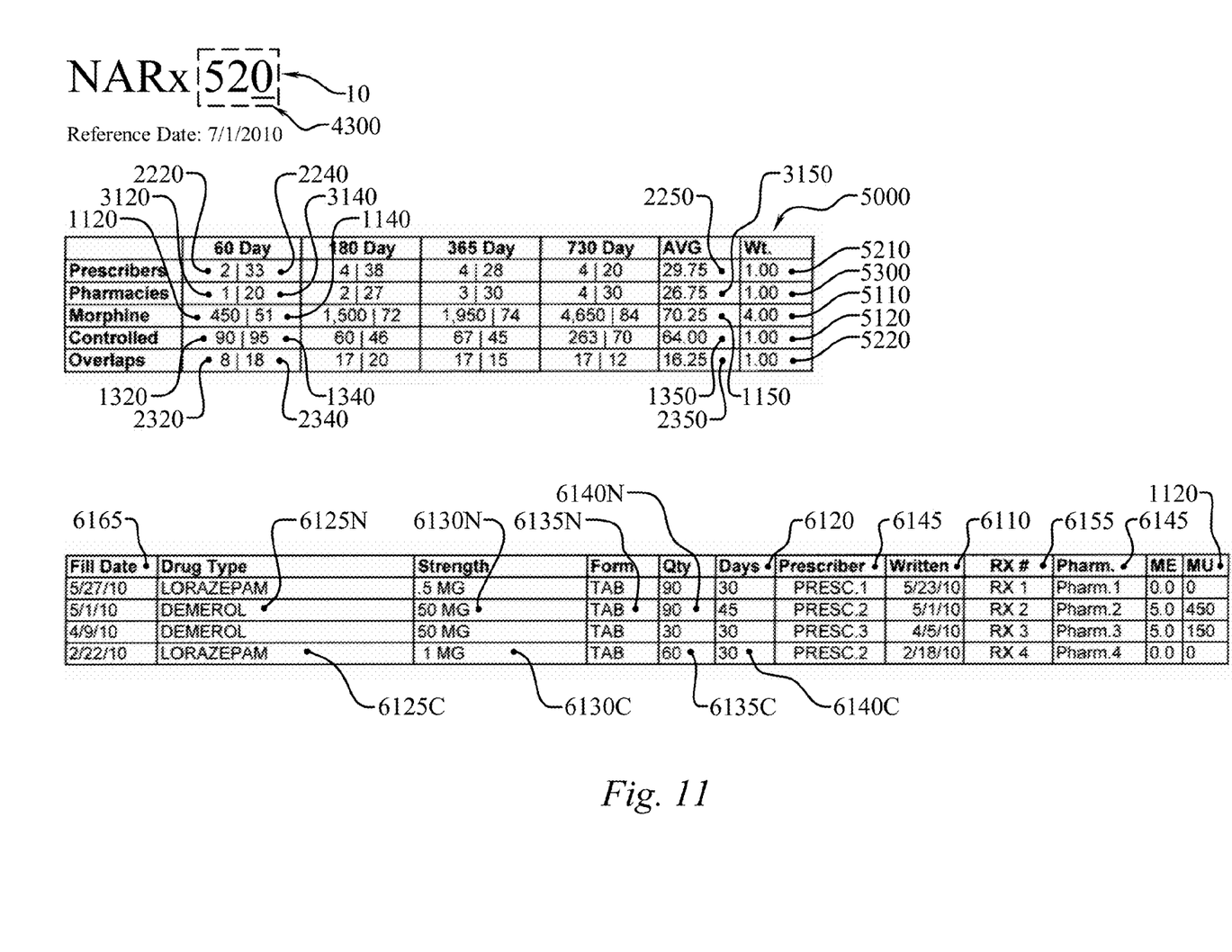
FIG. 11 shows a lower table representative of one embodiment's data that is retrieved from a patient record, and an upper table representative of several embodiments of indicators.

The upper table in FIG. 11 contains the actual values corresponding to the lower table, illustrating that in the past 60 days, the morphine equivalents unit period (1110), from the reference date of Jul. 1, 2010, the morphine equivalents unit quantity (1120) prescribed is 450; although it should be noted that the morphine equivalents unit quantity (1120) is not limited to the amount prescribed during the period but rather could be the amount consumed during the period. In this specific example, the morphine equivalents unit quantity (1120) places this patient in the fifty-first percentile, which is the morphine equivalents unit percentile (1140) displayed on the right side of the hash mark in the upper table of FIG. 11.

With reference again to FIG. 10, the instruction related indicator (2000) may include the step of identifying a potential prescription overlap situation when the record (6100) includes at least two prescribers (6145) during a prescription overlap period (2310). A prescription overlap indicator (2300) may then be created by determining a prescription overlap quantity (2320) that is the total number of days that the prescription period (6120) of the each prescriber (6145) coincide. Further, comparison of the prescription overlap quantity (2320) with the plurality of general population prescription drug use data yields a prescription overlap percentile (2340). For example, when the prescription overlap period (2310) is 60 days from the reference date of Jul. 1, 2010, as in FIG. 11, there were three prescriptions open within that period, only two of which are for narcotics. Therefore, within the prescription overlap period (2310) of 60 days, there were 8 days, namely May 1$^{st}$ through May 8$^{th}$, in which the two narcotic prescriptions for demerol overlapped. Therefore, the prescription overlap quantity (2320) is 8, as seen in the upper table of FIG. 11, which puts this patient in the eighteenth percentile, which is the prescription overlap percentile (2340). A high prescription overlap quantity (2320), or prescription overlap percentile (2340), is indicative of likely improper prescription drug use, particularly in cases where the prescription overlap quantity (2320) includes days in which a patient had multiple open prescriptions for the same narcotic originating from different prescribers. The prescription overlap indicator (2300) may be applied only to narcotic prescriptions, only to controlled substance prescriptions, or to both.

Another possible usage related indicator (1000) is a controlled substance unit indicator (1300). The controlled substance unit indicator (1300) is created in part by comparing the controlled substance quantity (6140C) with the plurality of general population prescription drug use data to determine a controlled substance unit percentile (1340) for a given controlled substance unit period (1310). Thus, in the upper table of FIG. 10, within the "Period A" column, which corresponds to the controlled substance unit period (1310), the row labeled "Controlled" contains the controlled substance unit quantity (1320), abbreviated CTRL Sub Qty in the table, on the left side of the hash mark, and the controlled substance unit percentile (1340), abbreviated CTRL Sub % in the table, on the right side of the hash mark.

The upper table in FIG. 11 contains the actual values corresponding to the lower table, illustrating that in the past 60 days, the controlled substance unit period (1310), from the reference date of Jul. 1, 2010, the controlled substance unit quantity (1320) prescribed is 90; although it should be noted that the controlled substance unit quantity (1320) is not limited to the amount prescribed during the period but rather could be the amount consumed during the period. In this specific example, the controlled substance unit quantity (1320) places this patient in the ninety-fifth percentile, which is the controlled substance unit percentile (1340) displayed on the right side of the hash mark in the upper table of FIG. 11.

Another possible instruction related indicator (2000) is a prescriber indicator (2200). The creation of a prescriber indicator (2200) is created in part by comparing a prescriber quantity (2220) with the plurality of general population prescription drug use data to determine a prescriber percentile (2240) for a given prescriber period (2210). Thus, in the upper table of FIG. 10, within the "Period A" column, which corresponds to the prescriber period (2210), the row labeled "Prescribers" contains the prescriber unit quantity (2220), abbreviated Prescriber Qty in the table, on the left side of the hash mark, and the prescriber percentile (2240), abbreviated Prescriber % in the table, on the right side of the hash mark.

The upper table in FIG. 11 contains the actual values corresponding to the lower table, illustrating that in the past 60 days, the prescriber period (2210), from the reference date of Jul. 1, 2010, the prescriber quantity (2220) is 2. In this specific example, the prescriber quantity (2220) places this patient in the thirty-three percentile, which is the prescriber percentile (2240) displayed on the right side of the hash mark in the upper table of FIG. 11.

In addition to the usage related indicator (1000) and the instruction related indicator (2000), the method may incorporate a dispensing related indicator (3000). The dispensing related indicator (3000) is created by comparing at least the patient information concerning the distributor (6155) with the plurality of general population prescription drug use data, and in this embodiment the adjustment factor (5000) is then applied to at least one of the usage related indicator (1000), the instruction related indicator (2000), and the dispensing related indicator (3000).

In one particular embodiment the dispensing related indicator (3000) is a distribution source indicator (3100). The creation of a distribution source indicator (3100) is created in part by comparing a distribution source quantity (3120) with the plurality of general population prescription drug use data to determine a distribution source percentile (3140) for a given distribution source period (3110). Thus, in the upper table of FIG. 10, within the "Period A" column, which corresponds to the distribution source period (3110), the row labeled "Pharmacies" contains the distribution source quantity (3120), abbreviated Dist Source Qty in the table, on the left side of the hash mark, and the distribution source (3140), abbreviated Dist Source % in the table, on the right side of the hash mark.

The upper table in FIG. 11 contains the actual values corresponding to the lower table, illustrating that in the past 60 days, the distribution source period (3310), from the reference date of Jul. 1, 2010, the distribution source quantity (3120) is 1. In this specific example, the distribution source quantity (3120) places this patient in the twentieth percentile, which is the distribution source percentile (3140) displayed on the right side of the hash mark in the upper table of FIG. 11.

Now that the first data column associated with the five rows of data in the upper tables of FIGS. 10 and 11 have been discussed, several additional steps will be explained; however, additional indicators will be discussed later. It should be noted again that all five indicators (2220, 3120, 1120, 1320, 2320) of these two figures are not required, rather this is merely one illustrative embodiment being explained in detail. In these figures three types of indicators have been examined, namely two usage related indicators (1000) including a morphine equivalents unit indicator (1100) and a controlled substance unit indicator (1300), two instruction related indicators (2000) including a prescriber indicator (2200) and a prescription overlap indicator (2300), and one dispensing related indicator (3000) that was a distribution source indicator (3100). As previously mentioned, an adjustment factor (5000) may be applied to any, or all, of these indicators to weight their relevance in predicting proper prescription drug use and ultimately arrive at a narcotics use indicator (10).

With specific reference to the embodiment of FIGS. 10 and 11 again, the adjustment factor (5000) is seen in the right column of the upper tables. In this embodiment each of the usage related indicators (1000) have a usage adjustment factor (5100), each of the instruction related indicators (2000) have a instruction adjustment factor (5200), and the dispensing related indicator (3000) has a dispensing adjustment factor (5300). Even further, as seen in the right column of the upper table of FIG. 11, in this one embodiment, the morphine equivalents unit indicator (1100) has a narcotic usage adjustment factor (5110), the controlled substance unit indicator (1300) has a controlled substance usage adjustment factor (5120), the prescriber indicator (2200) has a prescriber adjustment factor (5210), the prescription overlap indicator (2300) has an overlap adjustment factor (5220), and the distribution source indicator (3100) has a dispensing adjustment factor (5300). Here the narcotic usage adjustment factor (5110) is four times greater than the other adjustment factors because the morphine equivalents unit percentile (1140) is more directly indicative of improper prescription drug use.

Referring now to FIG. 11 and focusing only on the "60 Day" column and the "Wt." column, a narcotics use indicator (10) can be developed for this single period. For example, the narcotics use indicator (10) may be simply a weighted average of the five percentile values (2240, 3140, 1140, 1340, 2340). In this case, taking the sum of the prescriber percentile (2240) multiplied by the prescriber adjustment factor (5210), plus the distribution source percentile (3140) multiplied by the dispensing adjustment factor (5300), plus the morphine equivalents unit percentile (1140) multiplied by the narcotic usage adjustment factor (5110), plus the controlled substance unit percentile (1340) multiplied by the controlled substance usage adjustment factor (5120), plus the prescription overlap percentile (2340) multiplied by the overlap adjustment factor (5220); and dividing that sum by the sum of all the adjustment factors (5210, 5300, 5110, 5120, 5220) produces a number that is effectively a weighted percentile. In this example, the result would be [(33*1)+(20*1)+(51*4)+(95*1)+(18*1)]/(1+1+4+1+1)=46.25. For the convenience of a treating prescriber that requested the narcotics use indicator (10) this number may then be rounded to the nearest whole number which in this case is 46. In a further embodiment, it is likely that the treating prescriber would also like to immediately know the number of currently active prescriptions, yet still have a single convenient reference number, or score, to represent the likelihood of prescription drug abuse. Therefore, in this further embodiment, the number of active prescriptions is an active prescription indicator (4300) and is added as a third digit in the narcotics use indicator (10). In the example of FIG. 11, there are no active prescriptions, so the active prescription indicator (4300) is 0, which is applied to the end of the weighted percentile previously calculated to be 46 to arrive at a three digit narcotics use indicator (10) of 460. A treating prescriber can easily look at this narcotics use indicator (10) and quickly assess the likelihood that this particular patient is going to correctly utilize a prescription for a narcotic medication and/or a controlled substance. In this embodiment a patient with 9 or more active prescriptions would receive a three digit narcotics use indicator (10) of 469, which would immediately draw the attention of the prescriber, possibly warranting a more detailed review of the patient's prescription drug use. Thus, past patient prescription drug use data is transformed into a numerical narcotics use indicator (10) displayed on a visual media. The visual media may be a Cathode Ray Tube (CRT) monitor, a Liquid Crystal Display (LCD) monitor, a plasma monitor, a projector and screen, paper, and/or any other such visual display device known to those of ordinary skill in the art.

While the example above focused on a single period of time, FIG. 11 illustrates that the values just determined above may be determined for multiple periods. The upper table of FIG. 11 illustrates one embodiment in which 4 such periods are utilized. In such an embodiment, multi period percentiles may be determined for each indicator. Specifically, the "AVG" column of the table illustrates a multi period prescriber percentile (2250), a multi period distribution source percentile (3150), a multi period morphine equivalents unit percentile (1150), a multi period controlled substance percentile (1350), and a multi period prescriber overlap percentile (2350). In this embodiment, each of these multi period percentiles are simply the average percentile value for the given number of periods. Thus, the multi period prescriber percentile (2250) is simply the sum of the four individual period specific prescriber percentiles (2240) divided by the number of periods, in this case four, leading to (33+38+28+20)/4=29.75; and likewise for the other four indicators. Thus, the adjustment factors (5000) may be applied to these multi period percentiles in exactly the same manner as previously discussed to arrive at a weighted percentile. In this example, the result would be [(29.75*1)+(26.75*1)+(70.25*4)+(64*1)+(16.25*1)]/(1+1+4+1+1)=52.29. For the convenience of a treating prescriber that requested the narcotics use indicator (10) this number may then be rounded to the nearest whole number which in this case is 52. Then in the embodiment incorporating the active prescription indicator (4300), which remains at 0, the three digit narcotics use indicator (10) would be 520, as seen in FIG. 11. Therefore, in this particular example, looking at a two year time span rather than just a two month period raises the three digit narcotics use indicator (10) from 460 to 520. Obviously the lower table of FIG. 11 has been abbreviated and does not contain all of the prescriptions required to calculate the data for the 180 day period, the 365 day period, and the 730 day period, but the procedure is the same as just reviewed for the 60 day period.

A benefit of incorporating multiple periods is that because all the periods may have the same start date, i.e. the reference date in FIGS. 10 and 11, the data contained in the first period is also included in a second period, and likewise the data in the third period includes that in the first and the second period, and likewise the data in the fourth period includes that in the first period, second period, and third period. Therefore, in one embodiment of FIG. 11, namely when all four periods are considered, the morphine equivalents unit quantity (1120) of 450 when the morphine equivalents unit period (1110) is 60 days, is also included in the morphine equivalents unit quantity (1120) when the morphine equivalents unit period (1110)

is 180 days, 365 days, and 730 days. Therefore, in this embodiment the multi period morphine equivalents unit percentile (1150) is the average of the four periods wherein each period includes the morphine equivalents unit quantity (1120) from the first period; thus, the most recent data values are preferentially weighted. Although this preferential weighting is described above with respect to the multi period morphine equivalents unit percentile (1150), it may be applied to the determination of a multi period narcotic unit percentile (1250), a multi period controlled substance unit percentile (1350), a multi period prescription percentile (2150), a multi period prescriber percentile (2250), a multi period prescription overlap percentile (2350), a multi period distribution source percentile (3150), or a multi period distribution geography percentile (3250).

In another embodiment any of the adjustment factors may be automatically adjusted if preset criteria are met concerning data that highly correlates with improper prescription drug use. For example, as previously discussed with respect to FIG. 11, patients that have a prescription overlap quantity (2320) including days in which a patient had multiple open prescriptions for the same narcotic originating from different prescribers may flag an automatic adjustment to the overlap adjustment factor (5220) of at least twice the normal overlap adjustment factor (5220). Likewise, in another embodiment the prescriber adjustment factor (5210) may be automatically adjusted by a factor of at least two if a patient holds onto prescriptions from the same prescriber and then has them filled so that at least two controlled substance prescriptions are open at the same time based upon prescriptions for the same controlled substance by a single prescriber.

Figure 7:
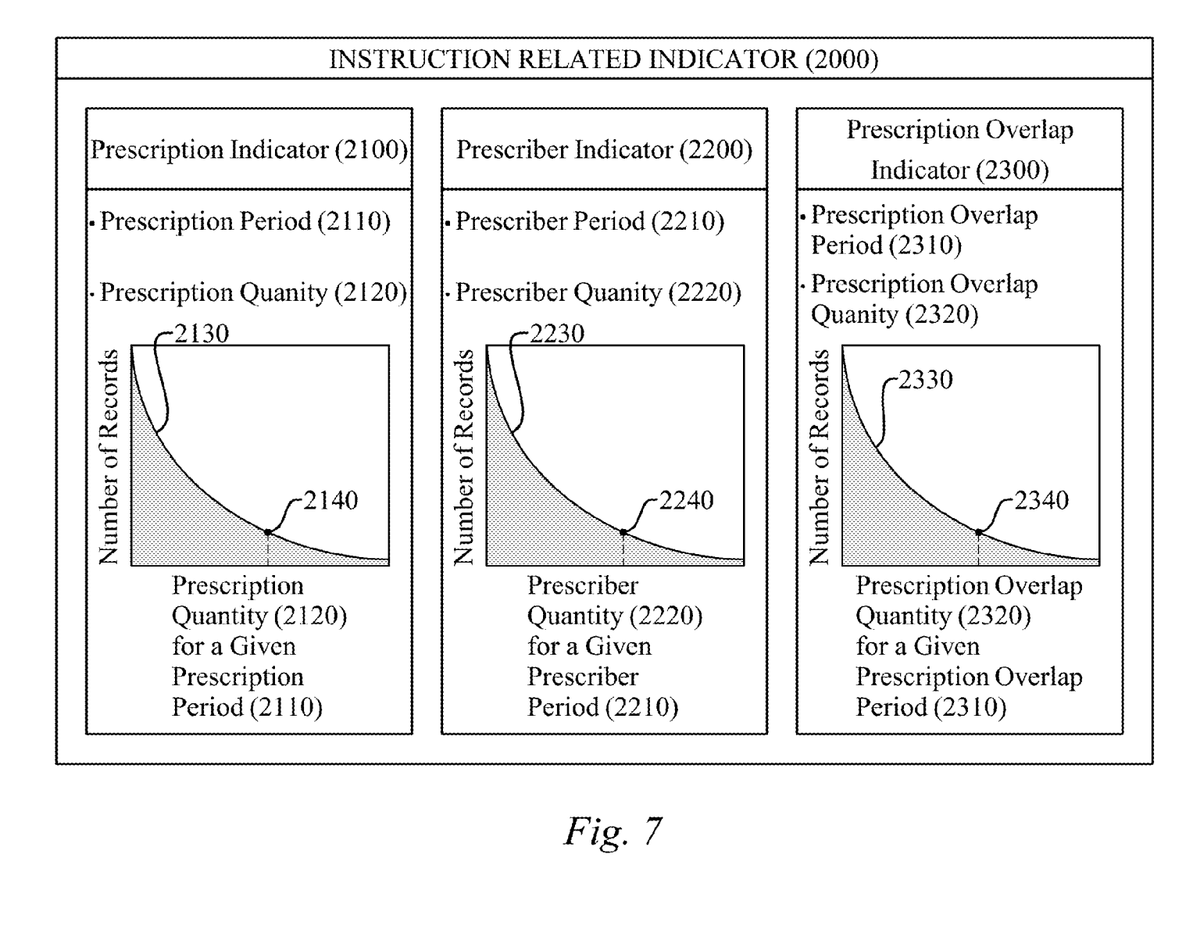
FIG. 7 shows a schematic diagram illustrating many potential instruction related indicator embodiments.

As seen in FIG. 7, yet another possible instruction related indicator (2000) is a prescription indicator (2100). The creation of a prescription indicator (2100) is created in part by comparing a prescription quantity (2120) with the plurality of general population prescription drug use data to determine a prescription percentile (2140) for a given prescription period (2110). Thus, one with skill in the art will recognize that this prescription indicator (2100) is yet another indicator that may be found in the upper tables of FIGS. 10 and 11 and weighted in the same manner previously discussed with respect to the other indicators to influence the narcotics use indicator (10). As such, the "Period A" column, would correspond to the prescription period (2110), and a row labeled "Prescriptions" would contain the prescription unit quantity (2120) on the left side of a hash mark, and the prescription percentile (2140) on the right side of the hash mark. Similarly, the instruction adjustment factor (5200) may include a prescription adjustment factor to weight the significance of the prescription indicator (2100) in the narcotics use indicator (10).

Figure 6:
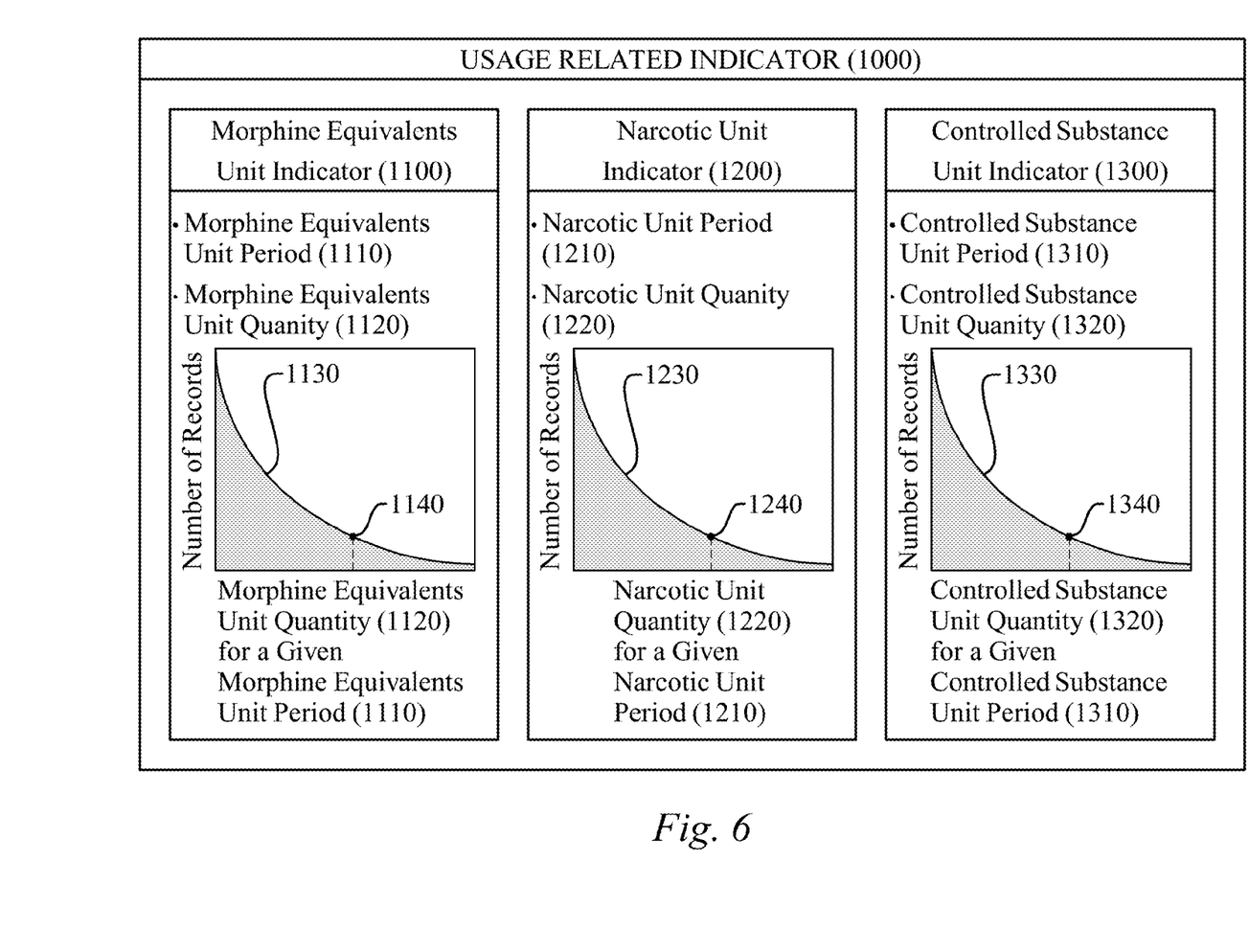
FIG. 6 shows a schematic diagram illustrating many potential usage related indicator embodiments.

Further, as seen in FIG. 6, another possible usage related indicator (1000) is a narcotic unit indicator (1200). The narcotic unit indicator (1200) is created in part by comparing the narcotic quantity (6140N) with the plurality of general population prescription drug use data to determine a narcotic unit percentile (1240) for a given narcotic unit period (1210). Thus, one with skill in the art will recognize that this narcotic unit indicator (1200) is yet another indicator that may be found in the upper tables of FIGS. 10 and 11 and weighted in the same manner previously discussed with respect to the other indicators to influence the narcotics use indicator (10). As such, the "Period A" column, would correspond to the prescription period (2110), and a row labeled "Narcotics" would contain the narcotic unit quantity (1220) on the left side of a hash mark, and the narcotic unit percentile (1240) on the right side of the hash mark. Similarly, the usage adjustment factor (5100) may include a narcotic unit adjustment factor to weight the significance of the narcotic unit indicator (1200) in the narcotics use indicator (10).

Figure 8:
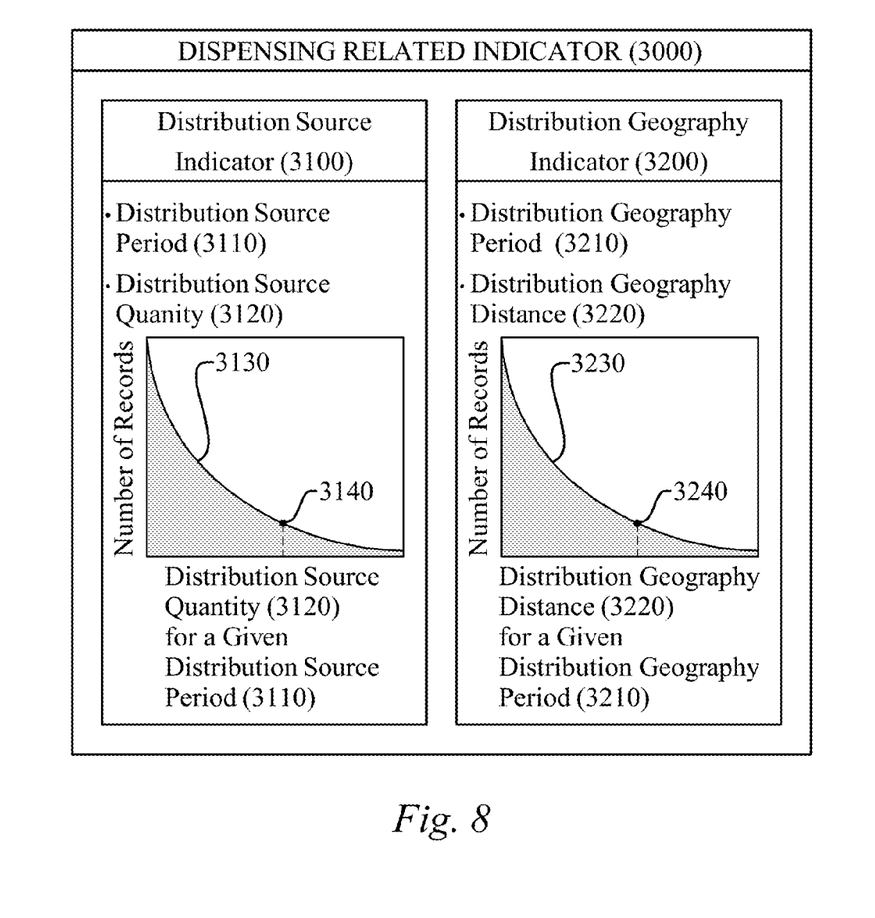
FIG. 8 shows a schematic diagram illustrating many potential dispensing related indicator embodiments.

As seen in FIG. 8, another embodiment includes a dispensing related indicator (3000) that is a distribution geography indicator (3200). The creation of a distribution geography indicator (3200) is created in part by comparing a distribution geography distance (3220) with the plurality of general population prescription drug use data to determine a distribution geography percentile (3240) for a given distribution geography period (3210). Thus, one with skill in the art will recognize that this distribution geography indicator (3200) is yet another indicator that may be found in the upper tables of FIGS. 10 and 11 and weighted in the same manner previously discussed with respect to the other indicators to influence the narcotics use indicator (10). As such, the "Period A" column, would correspond to the distribution geography period (3210), and a row labeled "Geography" would contain the distribution geography distance (3220) on the left side of a hash mark, and the distribution geography percentile (3240) on the right side of the hash mark. Similarly, the dispensing adjustment factor (5300) may include a distribution geography adjustment factor to weight the significance of the distribution geography indicator (3200) in the narcotics use indicator (10). In one embodiment the distribution geography distance (3220) is the total distance between the patient's home address and the location of the pharmacy, or pharmacies, that fills prescriptions during the distribution geography period (3210). In another embodiment the distribution geography distance (3220) is the distance between the locations of the pharmacies that fill prescriptions during the distribution geography period (3210). In yet another embodiment the distribution geography distance (3220) is the distance between the locations of only pharmacies that fill prescriptions for drugs within the same family during the distribution geography period (3210).

Figure 9:
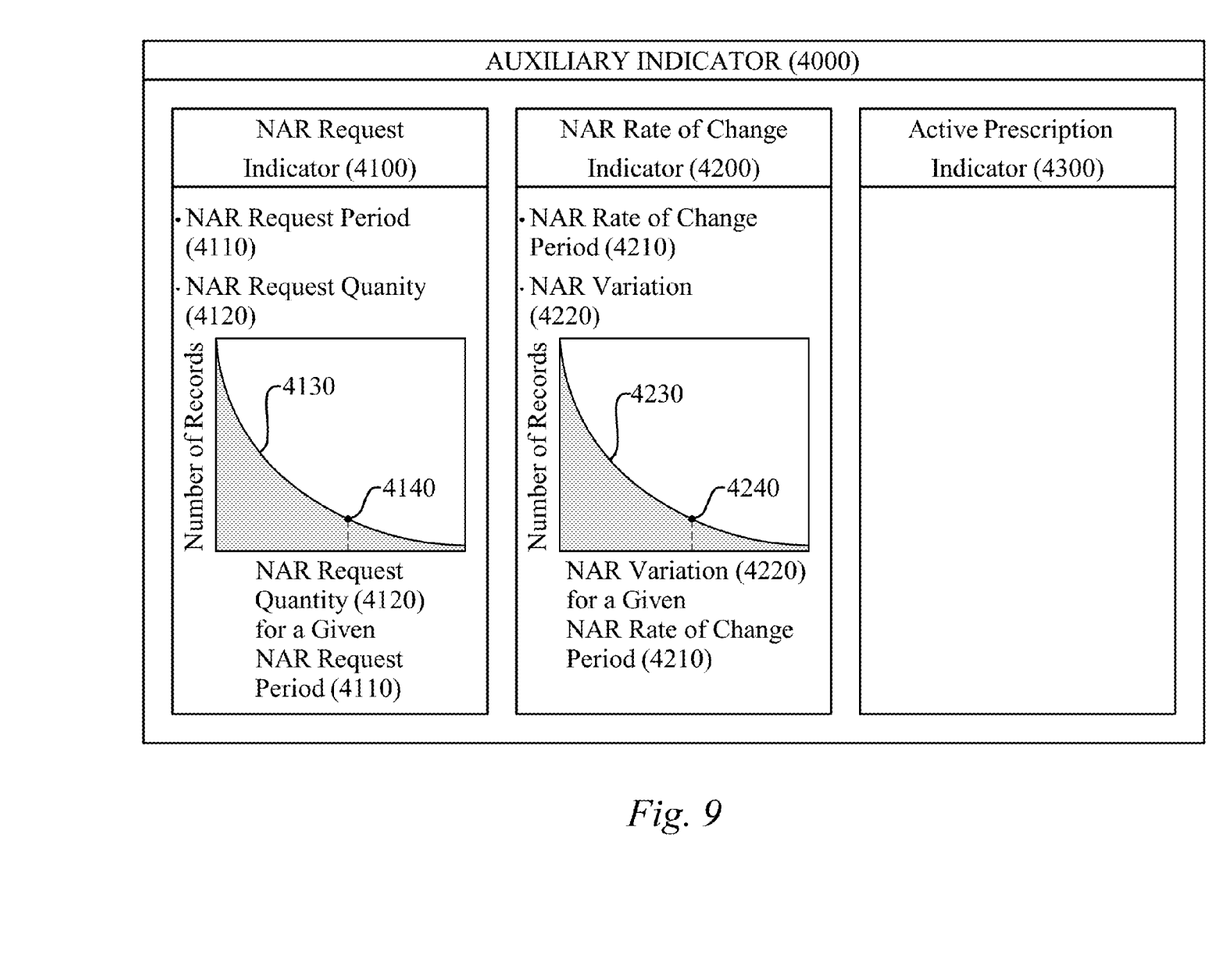
FIG. 9 shows a schematic diagram illustrating many potential auxiliary indicator embodiments.

As seen in FIGS. 5 and 9, another embodiment includes an auxiliary indicator (4000) that is a NAR request indicator (4100), The NAR request indicator (4100) is created in part by comparing the number of times, a NAR request quantity (4120), that a patient has had a narcotics use indicator (10) requested by a prescriber during a given period, namely a NAR request period (4110). The NAR request quantity (4120) may then be compared with the plurality of general population prescription drug use data to determine a NAR request percentile (4240) for the given NAR request period (4110). Thus, one with skill in the art will recognize that this NAR request indicator (4100) is yet another indicator that may be found in the upper tables of FIGS. 10 and 11 and weighted in the same manner previously discussed with respect to the other indicators to influence the narcotics use indicator (10). As such, the "Period A" column, would correspond to the NAR request period (4110), and a row labeled "NAR Requests" would contain the NAR request quantity (4120) on the left side of a hash mark, and the NAR request percentile (4140) on the right side of the hash mark. Similarly, an auxiliary indicator adjustment factor (5400) may include a NAR request adjustment factor to weight the significance of the NAR request indicator (4100) in the narcotics use indicator (10). In another embodiment, this NAR request adjustment factor may be automatically increased if the amount of narcotics use indicator (10) requests has exceeded a preset normal number of requests.

Even further, another embodiment includes an auxiliary indicator (4000) that is a NAR rate of change indicator (4200). The NAR rate of change indicator (4200) is created in part by comparing how the patient's narcotics use indicator (10) has changed over a period, or periods, of time to the rate of change associated with the plurality of general population prescription drug use data. For example, a request for a narcotics use indicator (10) may result in the determination of a first narcotics use indicator at a fixed time interval prior to the request date, and then the determination of a second narcotics risk indicator at a rate of change period (4210) prior to the fixed time interval. The difference between the first and second narcotics risk indicators, referred to as a NAR variation (4220), may then be used to adjust the presently requested narcotics use indicator if a threshold NAR variation (4220) is exceeded. The NAR variation (4220) may be compared with the plurality of general population prescription drug use data to determine a rate of change percentile (4240) for the given rate of change period (4210). Thus, one with skill in the art will recognize that this NAR rate of change indicator (4200) is yet another indicator that may be found in the upper tables of FIGS. 10 and 11 and weighted in the same manner previously discussed with respect to the other indicators to influence the presently requested narcotics use indicator (10). As such, the "Period A" column, would correspond to the rate of change period (4210), and a row labeled "Rate of Change" would contain the NAR variation (4220) on the left side of a hash mark, and the rate of change percentile (4240) on the right side of the hash mark. Similarly, the auxiliary indicator adjustment factor (5400) may include a rate of change adjustment factor to weight the significance of the NAR rate of change request indicator (4200) in the narcotics use indicator (10). In another embodiment, this NAR rate of change adjustment factor may be automatically increased if the NAR variation (4220) has exceeded a preset normal number of requests.

Throughout this document there are multiple references to a step of comparing a quantity, whether it is the 1120, 1220, 1320, 2120, 2220, 2320, 3120, 3220, 4120, or 4220 quantity, "with the plurality of general population prescription drug use data" to determine an indicator, whether it be a usage related indicator (1000), an instruction related indicator (2000), or a dispensing related indicator (3000). In some of the many disclosed embodiments the determination of an indicator includes a determination of whether the quantity is within an acceptable range or an unacceptable range, however other embodiments determine approximate percentile rankings of the quantity compared to the general population data, such as the 1140, 1240, 1340, 2140, 2240, 2340, 3140, 3240, 4140, or 4240 percentiles.

The general population prescription drug use data referenced is data associated with at least 1000 patients over the period of interest. In one embodiment this general population data is present in the database (6000) and is extracted for use in arriving at the indicators, or in some embodiments the percentile(s). The general population data need not be extracted each time patient specific data is retrieved from the database (6000); rather the general population data may be extracted after extended intervals, which may be months or even years. The general population prescription drug use data may be from a statewide or federal prescription database, a hospital specific prescription database, a commercial prescription database, or community specific prescription database. Thus, in yet another embodiment the general population prescription drug use data referenced is data associated with at least 1,000,000 patients over the period of interest; while yet a further embodiment, such as data used in generating FIGS. 10 and 11, utilizes data associated with at least 5,000,000 patients over the period of interest.

Therefore, the act of comparing a quantity "with the plurality of general population prescription drug use data" to determine an indicator may include the step of previously acquiring the general population prescription drug use data, processing the data, converting the data into a quickly accessible electronic format, and storing the converted data on hardware for use in determining the final narcotics risk indicator (10) in less than 5 seconds, whether the general population prescription drug data is local or on a hardware device on the other side of the planet. Thus, in one embodiment a local prescription drug use processor securely retrieves and stores into memory patient specific data from a remote database (6000), the local prescription drug use processor securely retrieves and stores into memory previously compiled and transformed data representative of the general populations prescription drug use, the local prescription drug use processor retrieves portions of this stored data to form and store at least a usage related indicator (1000) and an instruction related indicator (2000), the local prescription drug use processor applies an adjustment factor (5000) to at least one of usage and instruction related indicators (1000, 2000) and transforms them into a numerical narcotics use indicator (10), and the local prescription drug use processor formats and transmits the narcotics use indicator (10) to display on a visual media. Further, in light of confidential patient data security, the local prescription drug use processor may then clear the patient specific data from the local memory, as well as leave a timestamp within the remote database (6000) to serve as an indicator of when a patient's data was accessed. The prescription drug use processor may further securely transmit the narcotics use indicator (10) back to the database (6000) for storage and retrieval during subsequent data requests in determining updated narcotics use indicators (10). Thus, a system for carrying out the determination of a narcotics use indicator (10) may consist of several securely connected pieces of hardware communicating with the specially programmed prescription drug use processor to determine the narcotics use indicator (10). As the local prescription drug use processor retrieves the patient specific data from the database (6000), it may create a local patient-specific database for temporarily storing and processing data. The local patient-specific database is cleared of patient specific data upon the creation of the narcotics use indicator (10) and any associated reports that are simultaneously created.

Figure 1:
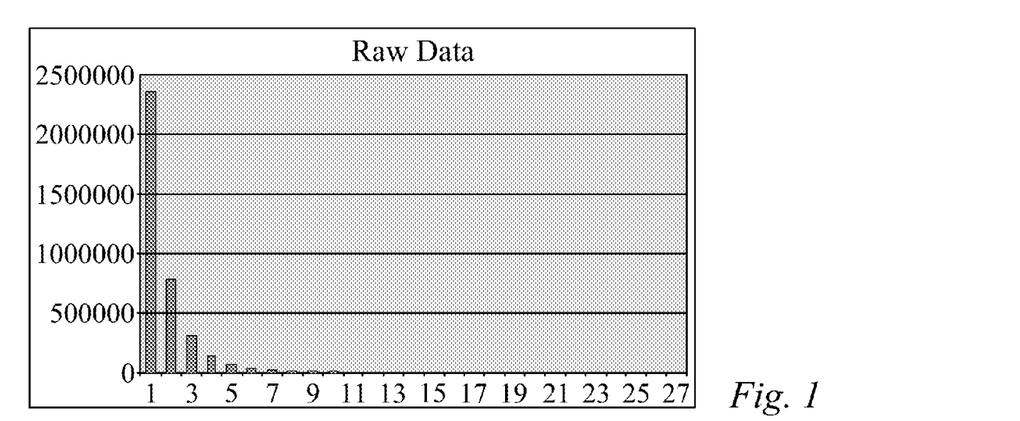
FIG. 1 shows an illustrative chart, not to scale, showing the number of patients on the y-axis and the number of prescribers on the x-axis.
Figure 2:
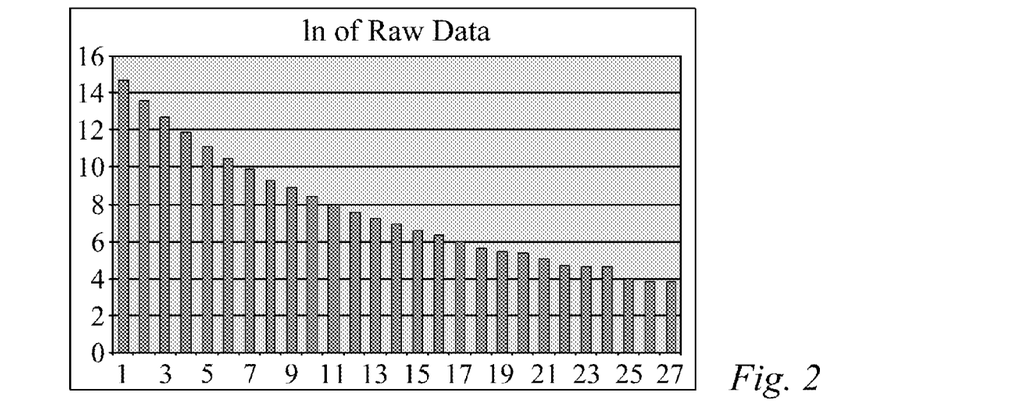
FIG. 2 shows an illustrative chart, not to scale, showing the natural log of the number of patients on the y-axis and the number of prescribers on the x-axis.
Figure 3:
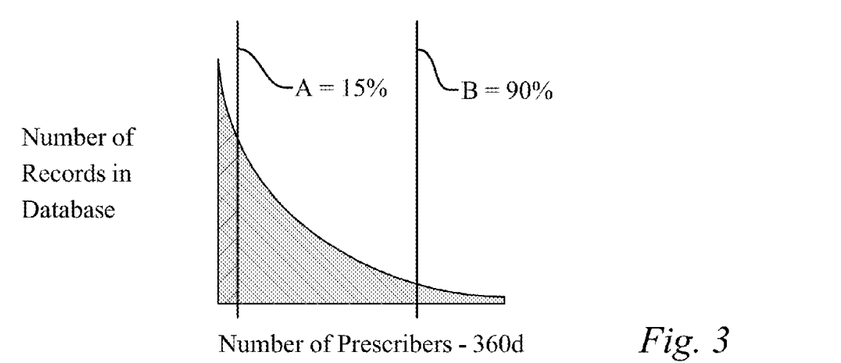
FIG. 3 shows an illustrative curve, not to scale, reflecting the data of FIG. 2 and FIG. 3.

The analysis of large quantities of data is well known in the field of statistics to identify acceptable ranges, unacceptable ranges, and percentile rankings, and therefore will not be reviewed in detail. However, one of many embodiments will be discussed for illustrative purposes. For instance, FIG. 1 illustrates raw data concerning the number of people in the general population drug use data on the y-axis, and the number of prescribers for a given period across the x-axis. It is clear from this figure that during this particular period, the overwhelming majority of patients only fill prescriptions from a single prescriber. A further embodiment determines a log normal distribution of the data, as seen in FIG. 2, which has the effect of straightening out the curve and spreading out the values. In this example, a log normal distribution may be preferred because using the raw data only would put a very small quantity of prescribers at the 99th percentile. This would mean that above this very small quantity of prescribers there would be no differentiation among patients. In yet another embodiment the raw data, or the log natural data, may be used to create a curve from which a percentile value is easily determined, as seen in FIG. 3. For example, the area under the curve seen in FIG. 3 and to the left of the line labeled "A" puts this number of prescribers in the $15^{th}$ percentile, whereas the position of the line labeled "B" puts this number of prescribers in the $90^{th}$ percentile. FIGS. 6-9 schematically illustrate similar analysis of data to produce one or more of the following curves, and one or more of the following percentiles; namely, morphine equivalents unit curve (1130), morphine equivalents unit percentile (1140), narcotic unit curve (1230), narcotic unit percentile (1240), controlled substance unit curve (1330), controlled substance unit percentile (1340), prescription curve (2130), prescription percentile (2140), prescriber curve (2230), prescriber percentile (2240), prescription overlap curve (2330), prescription overlap percentile (2340), distribution source curve (3130), distribution source percentile (3140)

The prescription drug use processor is a specially programmed computer device such as a personal computer, a portable phone, a multimedia reproduction terminal, a tablet, a PDA (Personal Digital Assistant), or a dedicated portable terminal that can perform the secure retrieval and processing of input, output, storage and the like of information. It goes without saying that such a program can be distributed through a recording medium such as a CD-ROM and a transmission medium such as the Internet. Further, the present invention may be a computer-readable recording medium such as a flexible disk, a hard disk, a CD-ROM, an MO, a DVD, a DVD-ROM, a DVD-RAM, a BD (Blu-ray Disc), flash drives, thumb drives, and a semiconductor memory that records the computer program. Thus, the distributed program may be used to program a computer to create a prescription drug processor thereby becoming a special purpose computer to securely perform particular functions pursuant to instructions from program software.

Numerous alterations, modifications, and variations of the preferred embodiments disclosed herein will be apparent to those skilled in the art and they are all anticipated and contemplated to be within the spirit and scope of this application. For example, although specific embodiments have been described in detail, those with skill in the art will understand that the preceding embodiments and variations can be modified to incorporate various types of substitute and or additional or alternative steps, procedures, and the order for such steps and procedures. Accordingly, even though only few variations of the present methodology and system are described herein, it is to be understood that the practice of such additional modifications and variations and the equivalents thereof, are within the spirit and scope of this application. The corresponding structures, materials, acts, and equivalents of all methods, means, and step plus function elements in the claims below are intended to include any structure, material, or acts for performing the functions in combination with other claimed elements as specifically claimed.

I claim:

1. A computer-implemented method for determining the likelihood of a proper prescription drug use by a patient, the method comprising:
    obtaining a record from a prescription database wherein the record i) is indicative of the prescription drug use by the patient and ii) includes a plurality of prescriptions filled by the patient, each prescription including at least a prescriber, a prescription drug type, a prescription drug strength, and a prescription drug quantity;
    generating, with one or more computer processors, a usage related indicator that indicates a ranking of a usage related quantity compared to a plurality of general population prescription drug use data, the usage related quantity based on at least the prescription drug type, the prescription drug strength, and the prescription drug quantity of two or more of the plurality of prescriptions;
    generating, with the one or more computer processors, an instruction related indicator that indicates a ranking of an instruction related quantity compared to a plurality of general population prescription drug instruction data, the instruction related quantity based on at least the prescriber of two or more of the plurality of prescriptions;
    applying, with the one or more computer processors, a weighted factor to at least one of the usage related indicator or the instruction related indicator to create an adjusted indicator; and
    generating, with the one or more computer processors, a prescription drug use indicator based on at least the adjusted indicator, the prescription drug use indicator including a number.

2. The method of claim 1,
    wherein the record includes a prescription for a narcotic;
    wherein the prescription drug type is a narcotic type, the prescription drug strength is a narcotic strength, and the prescription drug quantity is a narcotic quantity; and
    wherein generating the usage related indicator further includes the creation of a morphine equivalents unit indicator by transforming the narcotic type, the narcotic strength, and the narcotic quantity into a morphine equivalents unit quantity, and comparing the morphine equivalents unit quantity with the plurality of general population prescription drug use data to determine a morphine equivalents unit percentile for a given morphine equivalents unit period.

3. The method of claim 2, wherein applying the weighted factor further includes applying a usage weighted factor that is a narcotic usage weighted factor.

4. The method of claim 3, wherein the morphine equivalents unit percentile is determined for at least two morphine equivalents unit periods and the narcotic usage weighted factor is applied to a multi period morphine equivalents unit percentile that is the average of the morphine equivalents unit percentiles.

5. The method of claim 1,
    wherein the record includes a prescription for a controlled substance;
    wherein the prescription drug type is a controlled substance type, the prescription drug strength is a controlled substance strength, and the prescription drug quantity is a controlled substance quantity; and
    wherein generating the usage related indicator further includes the creation of a controlled substance unit indicator that indicates a ranking of the controlled substance quantity compared to the plurality of general population prescription drug use data to determine a controlled substance unit percentile for a given controlled substance unit period.

6. The method of claim 5, wherein applying the weighted factor further includes applying a usage weighted factor that is a controlled substance usage weighted factor.

7. The method of claim 6, wherein the controlled substance unit percentile is determined for at least two controlled substance unit periods and the controlled substance usage weighted factor is applied to a multi period controlled substance unit percentile that is the average of the controlled substance unit percentiles.

8. The method of claim 1, wherein the record contains a prescription period and wherein generating the instruction related indicator further includes identifying a potential prescription overlap situation when the record includes at least two prescribers during a prescription overlap period, and creating of a prescription overlap indicator by determining a prescription overlap quantity that is the total number of days that the prescription period of the each prescriber coincide and comparing the prescription overlap quantity with the plurality of general population prescription drug use data to determine a prescription overlap percentile.

9. The method of claim 8, wherein applying the weighted factor further includes applying an instruction weighted factor that is an overlap weighted factor.

10. The method of claim 9, wherein the prescription overlap percentile is determined for at least two prescription overlap periods and the overlap weighted factor is applied to a multi period prescription overlap percentile that is the average of the prescription overlap percentiles.

11. The method of claim 1, wherein generating the instruction related indicator further includes the creation of a prescriber indicator that indicates a ranking of a prescriber quantity compared to the plurality of general population prescription instruction use data to determine a prescriber for a given prescriber period.

12. The method of claim 11, wherein applying the weighted factor further includes applying an instruction weighted factor that is a prescriber weighted factor.

13. The method of claim 12, wherein the prescriber percentile is determined for at least two prescriber periods and the prescriber weighted factor is applied to a multiperiod prescriber percentile that is the average of the prescriber percentiles.

14. The method of claim 1, wherein each prescription includes a distributor, the method further comprising:
generating a dispensing related indicator that indicates a ranking of the distributor compared to the plurality of general population prescription drug dispensing data, and wherein the weighted factor is applied to at least one of the usage related indicator, the instruction related indicator, and the dispensing related indicator.

15. The method of claim 14, wherein generating the dispensing related indicator further includes the creation of a distribution source indicator that indicates a ranking of a distribution source quantity compared to the plurality of general population prescription drug dispensing data to determine a distribution source percentile for a given distribution source period.

16. The method of claim 15, wherein applying the weighted factor further includes applying a dispensing weighted factor.

17. The method of claim 16, wherein the distribution source percentile is determined for at least two distribution source periods and the dispensing weighted factor is applied to a multiperiod distribution source percentile that is the average of the distribution source percentiles.

18. A computer-implemented method for determining the likelihood of proper prescription drug use by a patient, the method comprising:
obtaining a record from a prescription database on a server wherein the record i) is indicative of the prescription drug use by the patient and ii) includes a plurality of prescriptions filled by the patient, each prescription including at least a prescriber, a narcotic type, a narcotic strength, a narcotic quantity, and a prescription period;
generating, with one or more computer processors, a usage related indicator that indicates a ranking of a morphine equivalents quantity compared to a plurality of general population prescription drug use data to determine a morphine equivalents unit percentile for a given morphine equivalents unit period, the morphine equivalents quantity based on at least the narcotic type, the narcotic strength, and the narcotic quantity of two or more of the plurality of prescriptions;
generating, with the one or more computer processors, an instruction related indicator based on:
a) identifying a potential prescription overlap situation of at least two prescribers during a prescription overlap period, and creating a prescription overlap indicator by determining a prescription overlap quantity that is the total number of days that the prescription period of the each prescriber coincide and comparing the prescription overlap quantity with the plurality of general population prescription drug instruction data to determine a prescription overlap percentile, and
b) creating of a prescriber indicator that indicates a ranking of a prescriber quantity compared to the plurality of general population prescription drug instruction data to determine a prescriber percentile for a given prescriber period, the prescriber quantity based on at least the prescriber of two or more of the plurality of prescriptions;
applying, with the one or more computer processors,
i) an overlap weighted factor to the prescription overlap percentile,
ii) a prescriber weighted factor to the prescriber percentile, and
iii) a narcotic usage weighted factor to the morphine equivalents unit percentile; and
transforming the sum of the weighted percentiles from (i), (ii), and (iii) into a narcotics use indicator, the narcotics use indicator including a number.

19. The method of claim 18, wherein the narcotics use indicator is at least a two digit number.

20. The method of claim 19, wherein the narcotics use indicator is at least a three digit number wherein the last digit i) is an active prescription indicator and ii) represents a number of active prescriptions.

21. The method of claim 18, wherein
(A) the prescription overlap percentile is determined for at least two prescription overlap periods and the overlap weighted factor is applied to a multiperiod prescription overlap percentile that is the average of the prescription overlap percentiles,
(B) the prescriber percentile is determined for at least two prescriber periods and the prescriber weighted factor is applied to a multi period prescriber percentile that is the average of the prescriber percentiles, and
(C) the morphine equivalents unit percentile is determined for at least two morphine equivalents unit periods and the narcotic usage weighted factor is applied to a multiperiod morphine equivalents unit percentile that is the average of the morphine equivalents unit percentiles.

22. The method of claim 21, wherein the at least one of the overlap weighted factor, the prescriber weighted factor, or the narcotic usage weighted factor automatically is increased when a preset criteria for at least one of the usage related indicator and the instruction related indicator, is retrieved from the database.

23. The method of claim 18, wherein the narcotic usage weighted factor is at least twice the overlap weighted factor, and the narcotic usage weighted factor is at least twice the prescriber weighted factor.

* * * * *